United States Patent
Steiner

(10) Patent No.: US 11,220,484 B2
(45) Date of Patent: Jan. 11, 2022

(54) PRODUCTION OF N-SUBSTITUTED AROMATIC HYDROXYLAMINE

(71) Applicant: SOLVIAS AG, Kaiseraugst (CH)

(72) Inventor: Heinz Steiner, Bubendorf (CH)

(73) Assignee: SOLVIAS AG, Kaiseraugst (CH)

(*) Notice: Subject to any disclaimer, the term of this patent is extended or adjusted under 35 U.S.C. 154(b) by 0 days.

(21) Appl. No.: 16/481,984

(22) PCT Filed: Jan. 30, 2018

(86) PCT No.: PCT/EP2018/052291
§ 371 (c)(1),
(2) Date: Jul. 30, 2019

(87) PCT Pub. No.: WO2018/141751
PCT Pub. Date: Aug. 9, 2018

(65) Prior Publication Data
US 2019/0389808 A1    Dec. 26, 2019

(30) Foreign Application Priority Data
Feb. 1, 2017  (EP) .................................. 17020041

(51) Int. Cl.
*C07D 231/22*  (2006.01)
*C07C 269/00*  (2006.01)
*C07D 257/06*  (2006.01)

(52) U.S. Cl.
CPC .......... *C07D 231/22* (2013.01); *C07C 269/00* (2013.01); *C07D 257/06* (2013.01)

(58) Field of Classification Search
CPC ...................................... C07D 231/22
See application file for complete search history.

(56) References Cited

U.S. PATENT DOCUMENTS

| 5,977,146 A | * | 11/1999 | Muller | C07D 213/76 514/352 |
| 8,642,780 B2 | * | 2/2014 | Dochnahl | C07C 271/28 548/371.1 |
| 10,377,720 B2 | * | 8/2019 | Suez | C07D 231/22 |

FOREIGN PATENT DOCUMENTS

WO    WO2016181386 A1    11/2016

OTHER PUBLICATIONS

Achim Porzelle et al., Facile Procedure for the Synthesis of N-Aryl-N-hydroxy Carbamates, Synlett, Feb. 24, 2009, 0798-0802, No. 5, Georg Thieme Verlag Stuttgart, New York.
Qiongyou Wu et al., Synthesis and Biological Activity of Novel Phenyltriazolinone Derivatives, Dec. 9, 2010, 9024-9034, Hubei, China.

* cited by examiner

*Primary Examiner* — Shawquia Jackson
(74) *Attorney, Agent, or Firm* — Nguyen Tarbet LLC

(57) ABSTRACT

An economic, one-step method for the production of N-substituted aromatic hydroxylamines of formula (I)

R—N(OH)—C(=O)—(O)R$_1$            (I), with hydrogen, by catalytic hydration with possibly modified hydration catalysts in an aprotic solvent and in the presence of a halogen formic acid ester and in some cases in the presence of a base.

20 Claims, No Drawings

PRODUCTION OF N-SUBSTITUTED AROMATIC HYDROXYLAMINE

The present invention concerns a method for production of N-alkoxycarbonyl- or N-aryloxycarbonyl-substituted aromatic hydroxylamines by catalytic hydration with hydrogen gas, and where applicable modified hydration catalysts, in an inert solvent and in the presence of a halogen formic acid ester and possibly a base.

N-substituted aromatic hydroxylamines are important chemicals, for example for the production of pesticides. Production takes place by means of a 2-stage reaction, i.e. firstly the aromatic hydroxylamine is produced, and in a second step this is substituted on nitrogen. Production of the arylhydroxylamine frequently takes place by means of catalytic hydration, catalytic transfer hydration (for example with a rhodium catalyst and hydrazine as the hydrogen donor) or by zinc reduction of nitro-aromatics. Often, secondary products form, such as aromatic amines and azoxy, azo and hydrazo compounds. Efforts have therefore been made to minimise the secondary reactions and hence improve the yields.

A. Porzelle et al. in Synlett 2009, No. 5, pages 798 to 802, describe the production of N-substituted hydroxylamines by means of a redox reaction. Nitro-aromatics are reduced with zinc and ammonium chloride, wherein the reaction mixture contains chloroformic acid ester, in order to capture the aromatic hydroxylamine by means of carbamate formation and suppress an over-reduction to amine. The reaction however is non-specific. Undesirable mixtures of various compositions of N-mono- and N,O-disubstituted hydroxylamines are formed. This method is not therefore suitable for production of N-substituted arylhydroxylamines on an industrial scale.

WO 2016/181386 describes the production of the intermediate product of formula A

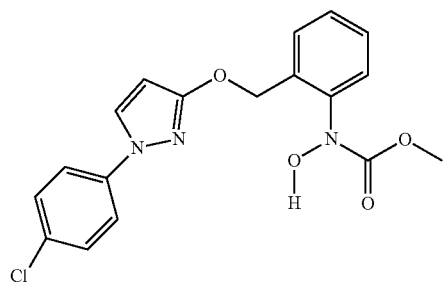
(A)

for the fungicide Pyraclostrobin by means of a two-stage process. The corresponding nitrogen compound is initially hydrated with a platinum catalyst in the presence of a nitrogen base and a sulphur compound with hydrogen, and in a second stage converted with chloroformic acid methylester. The method is not yet sufficiently economic since two successive chemical steps are required and the yield is not yet optimal.

There is a great need for an economic, direct catalytic hydration method for production of aromatic N-substituted hydroxylamines in a single process step, with which high selectivities and high yields can be achieved. Also it is highly desirable to avoid the accumulation of the frequently unstable and toxic arylhydroxylamines. The object of the present invention is to provide such a method.

It has now surprisingly been found that the presence of halogen formic acid esters is tolerated during the catalytic hydration of aromatic nitrogen compounds, i.e. the former are practically not hydrated, and such a method gives rise to very high selectivities and yields and leads to the desired N-substituted aromatic hydroxylamine. Secondary products, such as e.g. azoxy compounds, N-substituted aromatic amines or N,O-disubstituted arylhydroxylamines, are only formed to a low extent.

The object of the present invention is a method for production of N-substituted aromatic hydroxylamines of formula I:

wherein R is an aromatic residue and $R_1$ a hydrocarbon residue, by hydration of aromatic nitrogen compounds of formula II

wherein R has the meaning given above, with a hydration catalyst and hydrogen in an aprotic solvent, which is characterised in that the reaction is performed in the presence of at least stoichiometric quantities of a compound of formula III

wherein Y is halogen and $R_1$ has the meaning given above.

The group R may contain aromatic hydrocarbons or heteroaromatics, the ring systems of which may be condensed or linked and unsubstituted or substituted. Some examples of aromatic hydrocarbons are benzenes such as e.g. 2-nitrotoluene, naphthalene or anthracene, polycyclic hydrocarbons (also partly hydrated such as tetralin), biphenyl, cyclopentadienyl-anion and anthraquinone. Some examples of heteroaromatics are pyridines, pyrroles, azoles, diazines, triazines, triazoles, furans, thiophenes, oxazoles, indoles, quinolines, isoquinolines, carbazoles, purines, phtalazines, benztriazoles, benzofurans, quinazoles, acridines and benzothiophenes.

The group R may be substituted, also with substituents which in principle can also be hydrated. If such a reaction is desired, corresponding catalysts may be used. If not desired, either per se selective catalysts or modified catalysts may be used.

The group R may contain the same or different substituents such as halogen, hydroxyl, or a hydrocarbon residue bonded by way of a C-atom, O-atom, S-atom, N-atom, P-atom or Si-atom, or groups CO, C(O)O, SO, $SO_2$, for example one to six times, preferably one to four times, and particularly preferably one to two times, wherein hydrocarbon residues in the substituents may themselves be substituted. The cyclic residue R may also be provided with ring-forming substituents, for example $C_2$-$C_4$-alkylene, $C_2$-$C_4$-alkenylene, $C_4$-$C_8$-alkdienylene, $C_1$-$C_2$-alkylene diamino or $C_1$-$C_2$-alkylene dioxyl.

The substituents which may also be substituted may for example be $C_1$-$C_{12}$-alkyl, preferably $C_1$-$C_8$-alkyl and particularly preferably $C_1$-$C_4$-alkyl. Examples are methyl, ethyl, n- or i-propyl, n-, i- or t-butyl, pentyl, hexyl, octyl, decyl, undecyl and dodecyl.

The substituents which may also be substituted may for example be $C_3$-$C_8$-cycloalkyl, preferably $C_3$-$C_6$-cycloalkyl. Examples are cyclopentyl, cyclohexyl and cyclopropyl.

The substituents which may also be substituted may for example be $C_3$-$C_8$-cycloalkyl-alkyl, preferably $C_3$-$C_6$-cycloalkyl-alkyl with for example 1 to 4 C-atoms in alkyl.

Examples are cyclopentylmethyl, cyclohexylmethyl or -ethyl, and cyclopropylmethyl.

The substituents which may also be substituted may for example be $C_6$-$C_{18}$-aryl, for example phenyl or naphthyl, or heteroaryl, for example 2-methyl-2H-tetrazol-5-yl.

The substituents which may also be substituted may for example be $C_7$-$C_{12}$-aralkyl, for example benzyl or 1-phenyleth-2-yl.

The substituents which may also be substituted may for example be tri($C_1$-$C_4$-alkyl)-Si or triphenylsilyl. Examples of trialkylsilyl are trimethyl-, triethyl-, tri-n-propyl-, tri-n-butyl- and dimethyl-t-butylsilyl.

The substituents may for example be halogens. Examples are F and Cl.

The substituents which may also be substituted may for example be an aryloxy residue, alkyloxy residue, dialkylamino residue or alkylthio residue, wherein alkyl groups are $C_1$-$C_{12}$-alkyl, preferably $C_1$-$C_8$-alkyl and particularly preferably $C_1$-$C_4$-alkyl. Other possible residues are $C_5$-$C_8$-cycloalkyloxy or -thio, preferably $C_5$-$C_6$-cycloalkyloxy or -thio; ($C_5$-$C_8$-cycloalkyl)$_2$N—, $C_6$-$C_{18}$-aryloxy or -thio, and preferably $C_6$-$C_{10}$-aryloxy or -thio; or $C_7$-$C_{12}$-aralkyloxy-thio. Examples for the hydrocarbon residues in the substituents have been mentioned above.

The hydrocarbon residues of the substituents may themselves be substituted one or more times, for example one to three times, for example with halogen (F or Cl, particularly F), —N($C_1$-$C_4$-alkyl)$_2$, $C_1$-$C_4$-alkoxy, $C_1$-$C_4$-alkylthio, $C_5$-$C_6$-cycloalkyl, and substituted or unsubstituted rings such as e.g. phenyl, benzyl, phenoxy or 1H-pyrazol-3-yl) oxy.

Particularly preferably, R means 2-methylphenyl or 2-benzyl)oxy)-(1-(4-chlorophenyl)-3-)-1H-pyrazol-3-yl.

R1 as a hydrocarbon residue may preferably be residue selected from the group of linear or branched $C_1$-$C_8$-, preferably $C_1$-$C_6$- and particularly preferably $C_1$-$C_4$-alkyl, $C_4$-$C_8$- and preferably $C_3$-$C_6$-cycloalkyl, for example cyclopentyl or cyclohexyl, benzyl or phenyl.

Particularly preferably, $R_1$ means $C_1$-$C_4$-alkyl.

The compounds of formula III are halogen formic acid esters, wherein halogen preferably means bromine and in particular chlorine.

In a preferred embodiment, the compounds of formula III are $C_1$-$C_4$-alkyl-O—CO—Cl, quite particularly preferably chloroformic acid methylester.

Hydration may take place in the presence of an inert aprotic and apolar or polar solvent, wherein a solvent or mixture of solvents may be used. Suitable solvents are for example aliphatic, cycloaliphatic and aromatic hydrocarbons (pentane, hexane, petrolether, cyclohexane, methylcyclohexane, benzene, toluene, xylene), aliphatic and aromatic halogen hydrocarbons (dichloromethane, chloroform, chlorobenzene), nitriles (acetonitrile, propionitrile, benzonitrile), ethers (diethylether, dibutylether, diisopropylether, tert-butylmethylether, tert-butylethylether, t-amylmethylether, cyclopentyl methylether, ethylene glycol dimethylether, ethylene glycol diethylether, diethylene glycol dimethylether, tetrahydrofuran, 2-methyl tetrahydrofuran, dioxan, anisole), carbonic esters (dimethylcarbonate), carbonic acid esters and lactones (acetic acid methyl-, -ethyl- or -isopropylester, valerolactone), n-substituted lactames (n-methylpyrrolidon), carbonic acid amides (dimethylacetamide, n-methylpyrrolidon), acyclic ureas (n,n-dimethyl-2-imidazolidinon), sulphoxides (dimethyl sulphoxide) and sulphones (dimethylsulphone, tetramethylene sulphone). Water may also be added to the reaction mixture, for example in a quantity of up to 50% by weight, and preferably up to 20% by weight relative to the quantity of solvent. Preferred solvents are ethers, hydrocarbons, halogenated hydrocarbons, carbonic acid esters, carbonates and amides. Particularly preferred are ethers, in particular tetrahydrofuran, 2-m ethyltetrahydrofuran, cyclopentylmethylether, tert-butylmethylether, tert-butylethylether and tert-amylmethylether, and carbonates, in particular dimethylcarbonate.

Suitable catalysts may be (commercial) noble metal catalysts or also base metal catalysts. Suitable noble metals are ruthenium, rhodium, iridium, palladium and platinum. Palladium and in particular platinum are preferred. The noble metals are usually applied to carrier materials and contain for example up to 20 w. % noble metal relative to the carrier material. Carrier materials are in particular carbon, metal oxides and silicates. Suitable base metal catalysts usually consist of nickel or cobalt, which may be applied to a carrier material e.g. silicon dioxide. Recently also, methods have been disclosed for production of catalysts in the form of nanoparticles, either noble metal or base metal catalysts. Such catalysts may also be used in the method according to the invention.

The catalysts are normally used in quantities of 0.1 to 10% by weight, more preferably 0.1 to 5% by weight relative to the substrate.

Most commercial catalysts hydrate the aromatic nitrogen group to the amino group, without forming arylhydroxylamine in high selectivity. It has now been found that the further hydration of the intermediate arylhydroxylamine may be eliminated if the catalytic hydration is carried out in the presence of a halogen formic acid ester. The presence of a halogen formic acid ester and the in-situ conversion of the hydroxylamino group into a N-alkoxycarbonyl- or N-aryloxycarbonyl-hydroxylamino group evidently leads to a greatly reduced hydrogenolysis capacity of the N—O bond, and hence to a greatly increased selectivity. Surprisingly, even with the use of catalysts which normally hydrate nitro-aromatics into arylhydroxylamines without high selectivity, high selectivities are obtained on N-substituted arylhydroxylamines.

Halogen formic acid esters have a similar reactivity to carbonic acid halogenides, which can very easily be converted into aldehydes by catalytic hydration. It is therefore surprising and could not be foreseen that halogen formic acid esters are not themselves significantly hydrated during the catalytic hydration of aromatic nitrogen compounds according to the invention. Therefore it is possible to use halogen formic acid esters in stoichiometric to slightly super-stoichiometric quantities. It is also possible to add the halogen formic acid esters in portions or continuously depending on the conversion.

Evidently, per se selective or modified catalysts may be used which are suitable for stopping the hydration of the nitrogen group at the stage of arylhydroxylamines. Examples of such modifiers are sulphur compounds (for example sulphoxides, thioethers, thiols, thiourea, thiophene), phosphorus compounds (for example phosphines, phosphine oxides, phosphoric and phosphonic acids or esters), where applicable in combination with acids (acetic acid, methane sulphonic acid) or tertiary amines (N-methylmorpholin, tetramethylene ethylenediamine). Dimethyl sulphoxide and in particular hypophosphoric acid are preferred.

Hypophosphoric acid may for example be used in the ratio of 0.01-20 to 1 catalyst part by weight, preferably in the ratio of 0.1-5 to 1 catalyst part by weight.

Dimethyl sulphoxide may for example be used in the ratio of 0.1-20 to 1 part by weight, preferably 1-6 to 1 catalyst part by weight.

The combination of a hydration catalyst which is as selective as possible and in some cases modified, with the use of a halogen formic acid ester during hydration, leads to particularly high selectivity relative to the suppression of the hydrogenolysis of the N—O bond and the formation of azoxy or hydrazo compounds.

In the method according to the invention, hypophosphoric acid $H_3PO_2$ or dimethyl sulphoxide (DMSO) or a combination thereof is used as a modifier, because by the addition thereof, the desired aryl-N(OH)COOR is obtained in particularly high selectivity and yield. The further hydration of the arylhydroxylamines and aryl-N(OH)COOR is thereby particularly greatly suppressed without the hydration activity being surplusively reduced. Also, $H_3PO_2$ and DMSO—in contrast to modifiers from the group "ammonium, primary and secondary amines"—tolerate the use of a halogen formic acid ester because, in contrast to said nitrogen compounds, the former do not react therewith.

The use of $H_3PO_2$ as a modifier is also particularly attractive because, on use of noble metal catalysts modified with hypophosphoric acid, the catalytic hydration of other functionalities is particularly greatly inhibited (see EP-B1-0 931 053). Thus N-substituted arylhydroxylamines may be produced which are not only practically free from N-substituted arylamines and azoxy and hydrazo compounds, but also with the greatest possible retention of further hydratable functionalities.

A preferred embodiment of the method according to the invention is characterised in that hypophosphoric acid $H_3PO_2$ and/or DMSO are used as a modifier.

A further particularly preferred embodiment of the method according to the invention is characterised in that as a catalyst, platinum on carbon (Pt/C) is used in combination with hypophosphoric acid $H_3PO_2$ and/or DMSO.

The reaction temperature is for example preferably −20° C. to 100° C. and particularly preferably 0° C. to 60° C.

The hydrogen pressure may be up to 100 bar, and preferably 1 to 20 bar.

The reaction may be performed in the presence of inorganic bases, such as for example sodium hydrogen carbonate, sodium carbonate, sodium hydroxide, sodium phosphate, potassium phosphate, disodium hydrogen phosphate, dipotassium hydrogen phosphate, or tertiary nitrogen bases such as for example triethylamine, but also with combinations of bases in order to capture acids of formed hydrogen halides.

Stoichiometric quantities may be used relative to the halogen formic acid ester, or also a surplus. Preferably, inorganic bases are used. Particularly preferably, weak inorganic bases are used, such as disodium or dipotassium hydrogen phosphate or sodium hydrogen carbonate. Also, the combination of bases is particularly preferred, wherein a weak base, for example disodium hydrogen phosphate, is present in sub-stoichiometric quantity, and another base, for example watery potassium hydroxide solution, is added in portions or continuously depending on the conversion.

A quite particularly preferred embodiment of the method according to the invention serves to produce an intermediate product of formula A of the fungicide Pyraclostrobin

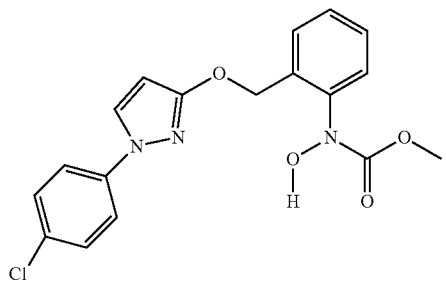

by hydration of the corresponding nitrogen compound of formula B

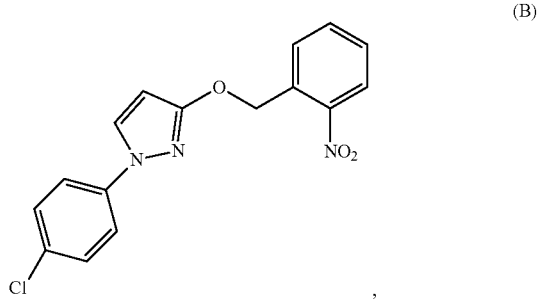 [SMILES: O=[N+]([O-])c1ccccc1COc1ccn(-c2ccc(Cl)cc2)n1]

with hydrogen in the presence of a hydration catalyst in an inert solvent and in the presence of an inorganic base, which is characterised in that it is performed in the presence of at least stoichiometric quantities of a halogen formic acid ester of the formula $C_1$-$C_4$-alkyl-O—C(=O)-hal.

A further, quite particularly preferred embodiment of the method according to the invention serves for the production of methyl hydroxy(o-tolyl) carbamate by hydration of 2-nitrotoluene with hydrogen in the presence of a hydration catalyst in an inert solvent and in the presence of a base, which is characterised in that it is performed in the presence of at least stoichiometric quantities of a halogen formic acid ester of formula $C_1$-$C_4$-alkyl-O—C(=O)-hal.

The method according to the invention is generally performed such that the nitrogen compound and the halogen formic acid ester are presented with the solvent. Then the catalyst and where applicable the base are added. It is however easily also possible to proceed in the reverse order. Accordingly, hydrogen is applied and the reaction started. The reaction development may be monitored by the hydrogen consumption. When no further hydrogen is consumed, the method is ended. It is also easily possible to provide no base, or only a sub-stoichiometric quantity of a base, and add further quantities of the same base or another base depending on the conversion, in order to guarantee the obtaining of a favourable pH range. The halogen formic acid ester may also be added depending on the conversion. The reaction mixture is then processed in the known fashion, such as for example filtration, extraction, distillation or crystallisation. The method may be performed continuously or in batches in various reactor types.

The N-substituted compounds which can be produced according to the invention are either directly active substances or intermediate products for production of such substances, particular in the field of production of aromatics and perfumes, pharmaceuticals and agrochemicals, and technical products such as colourings, pigments and additives. The direct production of the commercial product Pyraclostrobin has already been mentioned above.

The following examples explain the invention.

Example 1: Production of Methyl Hydroxy(Phenyl) Carbamate 50 mg 5% Pt-carbon catalyst is placed in a glass vessel with 15 mg 50% watery hypophosphoric acid and 1 ml deionised water, and agitated for 10 minutes.

In a Parr® glass flask, 1.04 g nitrobenzene is placed in 30 ml cyclopentyl methylether, and 1.68 g (1.4 equivalent) disodium hydrogen phosphate and 1.04 g (1.3 equivalent) chloroformic acid methylester added. The catalyst suspension is then rinsed with 4 ml deionised water in the Parr® glass flask, and hydrated for 3 hours at a temperature of 22° C. and a hydrogen pressure of 4 bar. After rendering the apparatus inert with nitrogen, 1 ml methanol is added and agitated for 15 minutes to destroy the surplus chloroformic acid methylester. Then the solids are filtered out and washed with 20 ml cyclopentyl methylether. The filtrate is dried over sodium sulphate and evaporated in a vacuum at 60° C. This produces 1.43 g (101% of theoretically possible) methyl hydroxy(phenyl) carbamate with a purity of 91.7% (yield 92.6%), which still contains 8.3% methyl phenyl carbamate (determined by HPLC (220 nm)).

Example 2: Production of Methyl (2-(((1-(4-Chlorophenyl)-1H-Pyrazol-3-Yl)Oxy)Methyl)Phenyl) (Hydroxy) Carbamate 83 mg 5% Pt-carbon catalyst is placed in a glass vessel with 164 mg 50% watery hypophosphoric acid and 1 ml deionised water and agitated for 10 minutes.

1.65 g 1-(4-chlorophenyl)-3-((2-nitrobenzyl)oxy)-1H-pyrazol is placed in 30 ml cyclopentylmethylether in a Parr® glass flask, and 0.994 g (1.4 equivalent) disodium hydrogen phosphate and 0.614 g (1.3 equivalent) chloroformic acid methylester are added. The catalyst suspension is then rinsed with 4 ml deionised water in the Parr® glass flask and hydrated for 7 hours at a temperature of 22° C. and a hydrogen pressure of 4 bar. After rendering the apparatus inert with nitrogen, 1 ml methanol is added and agitated for 15 minutes in order to destroy the surplus chloroformic acid methylester. Then the solids are filtered out and washed with 20 ml cyclopentyl methylether. The filtrate is dried over sodium sulphate and evaporated in a vacuum at <1 mbar and 60° C. This gives 1.80 g beige solid consisting of methyl (2-(((1-(4-chlorophenyl)-1H-pyrazol-3-yl)oxy)methyl)phenyl)(hydroxy) carbamate with a purity of 97% according to HPLC (220 nm), which according to HPLC and LC-MS still contains 3% methyl (2-(((1-(4-chlorophenyl)-1H-pyrazol-3-yl)oxy)methyl)phenyl) carbamate. This represents a yield of 93% of the theoretically possible.

Example 3: Production of Methyl (2-(((1-(4-Chlorophenyl)-1H-Pyrazol-3-Yl)Oxy)Methyl)Phenyl) (Hydroxy) Carbamate 1086 mg 5% Pt-carbon catalyst (water content: 54%) is placed in a glass vessel with 3 ml deionised water and 550 mg 50% watery hypophosphoric acid, and agitated for 10 minutes.

In a 100 ml agitation autoclave, 10.00 g 1-(4-chlorophenyl)-3-((2-nitrobenzyl)oxy)-1H-pyrazol is placed in 50 ml 2-methyl tetrahydrofuran, and 6.03 g (1.4 equivalent) disodium hydrogen phosphate and 3.73 g (1.3 equivalent) chloroformic acid methylester are added. The catalyst suspension is then rinsed with 2 ml deionised water in the autoclave and hydrated at a temperature of 21° C. and a hydrogen pressure of 7 bar. After 1.5 hours, the hydrogen absorption stops. After rendering the apparatus inert with nitrogen, 1 ml methanol is added and agitated for 20 minutes in order to destroy the surplus chloroformic acid methylester. The reaction mixture is then rinsed with 20 ml 2-MeTHF and 5 ml water from the autoclave, and the catalyst filtered out. The watery phase is separated in the separation funnel. The organic phase is washed with 3 ml water and, after separation of the watery phase, dried over sodium sulphate, filtered and evaporated in the rotary evaporator at 60° C. The residue is dried for 1 hour at 80° C./<1 mbar. 11.06 g beige solid is isolated with a purity of 98.4% according to HPLC (254 nm), corresponding to a yield of 96%. The solid is dissolved in 40 ml 2-methyl tetrahydrofuran at 60° C., 30 ml of this is then distilled off and the resulting solution cooled under agitation to 15° C. After 30 minutes' agitation, the resulting crystals are filtered under suction and washed with 10 ml cold 2-MeTHF. This gives 9.46 g re-crystallised methyl (2-(((1-(4-chlorophenyl)-1H-pyrazol-3-yl)oxy)methyl)phenyl)(hydroxy) carbamate with a purity of 100% according to HPLC (220 nm and 254 nm). The parent lye is evaporated and the residue dried for one hour at 80° C./<1 mbar. This gives 1.54 g of a reddish solid which, according to HPLC (220 nm), contains 86.8% methyl (2-(((1-(4-chlorophenyl)-1H-pyrazol-3-yl)oxy)methyl)phenyl)(hydroxy) carbamate and 9.8% methyl (2-(((1-(4-chlorophenyl)-1H-pyrazol-3-yl)oxy)methyl)phenyl) carbamate.

Example 4: Production of Methyl Hydroxy(O-Tolyl) Carbamate 38 mg 5% Pt-carbon catalyst (water content: 54%) is placed in a 22 ml glass vial with 0.7 ml deionised water and 19 mg 50%, watery hypophosphoric acid and agitated for 10 minutes. Then 3.4 ml tetrahydrofuran, 343 mg 2-nitrotoluene, 497 mg disodium hydrogen phosphate and 307 mg methyl chloroformate were added. After flushing with argon and hydrogen, the mixture is agitated for 7 hours under 6 bar hydrogen at 25° C. The organic phase is then analysed by means of HPLC and LC-MS. this shows 90% methyl hydroxy(o-tolyl) carbamate and 7% methyl (o-tolyl) carbamate, and 3% of an unknown secondary product (area %, UV 220 nm).

Examples 5-11: Production of Methyl Hydroxy(O-Tolyl) Carbamat

In the same way as example 4, various solvents were tested.

The table below shows the results of the HPLC analysis (area % at 220 nm) of the organic phase.

| Example | Solvent | Conversion | Methyl hydroxy(o-tolyl) carbamate | Ratio of methyl hydroxy(o-tolyl) carbamate to methyl (o-tolyl) carbamate |
|---|---|---|---|---|
| 4 | THF | 100% | 90 | 93/7 |
| 5 | 2-MeTHF | 100% | 85 | 87/13 |
| 6 | cyclopentyl methylether | 100% | 76 | 79/21 |

| Example | Solvent | Conversion | Methyl hydroxy(o-tolyl) carbamate | Ratio of methyl hydroxy(o-tolyl) carbamate to methyl (o-tolyl) carbamate |
|---|---|---|---|---|
| 7 | tert-butyl methylether | 100% | 73 | 76/24 |
| 8 | iso-propylacetate | 100% | 66 | 78/22 |
| 9 | chlorobenzene | 92% | 19 | 63/37 |
| 10 | 2-butanone | 100% | 48 | 14/86 |
| 11 | acetone | 80% | 38 | 6/94 |

Example 6: Production of Methyl (2-(((1-(4-Chlorophenyl)-1H-Pyrazol-3-Yl)Oxy)Methyl)Phenyl) (Hydroxy) Carbamate 545 mg 5% Pt-carbon catalyst (water content: 58%) are placed in a glass vessel with 3 ml deionised water and 550 mg 50% watery hypophosphoric acid, and agitated for 10 minutes.

In a 100 ml agitation autoclave, 10.00 g 1-(4-chlorophenyl)-3-((2-nitrobenzyl)oxy)-1H-pyrazol is placed in 30 ml dimethyl carbonate, and 6.03 g (1.4 equivalent) disodium hydrogen phosphate and 3.73 g (1.3 equivalent) chloroformic acid methylester added. The catalyst suspension is then rinsed with 2 ml deionised water in the autoclave and hydrated at a temperature of 15-20° C. and a hydrogen pressure of 15 bar. After 5 hours, the hydrogen absorption stops. After rendering the apparatus inert with nitrogen, 1 ml methanol and 30 ml dimethyl carbonate are added and agitated for 20 minutes in order to destroy the surplus chloroformic acid methylester. It is then heated to 80° C. to ensure that all product has dissolved. It is then cooled to 55° C. and the reaction mixture is rinsed with 20 ml dimethyl carbonate and 5 ml water from the autoclave, and the catalyst filtered off. The watery phase is separated in the separation funnel. The organic phase is washed with 3 ml water and, after separation of the watery phase, dried over sodium sulphate, filtered and evaporated in the rotary evaporator at 60° C. The residue is dried for one hour at 80° C./<1 mbar. 11.06 g beige solid is isolated with a purity of 95% according to HPLC (220 nm and 254 nm), corresponding to a yield of 93%.

Example 7: Production of Methyl Hydroxy(3-(2-Methyl-2H-Tetrazol-5-Yl)Phenyl) Carbamate 83 mg 5% Pt-carbon catalyst (water content: 58%) are placed in a glass vessel with 164 mg 50% watery hypophosphoric acid and 1 ml deionised water, and agitated for 10 minutes.

1.25 g 2-methyl-5-(3-nitrophenyl)-2H-tetrazole is placed in a Parr® glass flask with 12.5 ml 2-methyl tetrahydrofuran, and 1.15 g (1.4 equivalent) disodium hydrogen phosphate and 0.71 g (1.3 equivalent) chloroformic acid methylester are added. The catalyst suspension is then rinsed with 4 ml deionised water in the Parr® glass flask and hydrated at a temperature of 15° C. and a hydrogen pressure of 4 bar. After 15 minutes, the hydration stops. After rendering the apparatus inert with nitrogen, 0.5 ml methanol is added and agitated for 15 minutes to destroy the surplus chloroformic acid methylester. Then the solids are filtered off and washed with 20 ml 2-methyl tetrahydrofuran. After phase separation, the organic phase is dried over sodium sulphate and evaporated in a vacuum at <1 mbar and 60° C. This gives 1.46 g beige solid consisting of methyl hydroxy(3-(2-methyl-2H-tetrazol-5-yl)phenyl) carbamate (according to LC-MS) with a purity of 98% according to HPLC (220 nm), corresponding to a yield of 98% of the theoretically possible.

Example 8: Production of Benzyl Hydroxy(O-Tolyl) Carbamate 70 mg 5% Pt-carbon catalyst (water content: 58%) is placed in a 22 ml glass vial with 1 ml deionised water and 35 mg 50% watery hypophosphoric acid, and agitated for 10 minutes. Then 10 ml tetrahydrofuran, 823 mg 2-nitrotoluene, 1.19 g disodium hydrogen phosphate and 1.4 g benzyl chloroformate are added. After flushing with argon and hydrogen, the mixture is shaken for 5 hours at 5 bar hydrogen at 15° C. After rendering the apparatus inert with nitrogen, 0.5 ml methanol is added and agitated for 15 minutes in order to destroy the surplus chloroformic acid benzylester. Then the solids are filtered off and washed with 10 ml 2-tetrahydrofuran. After phase separation, the organic phase is dried over sodium sulphate and evaporated in a vacuum at <1 mbar and 60° C. This gives 1.57 g light beige oil consisting of benzyl hydroxy(o-tolyl) carbamate (according to LC-MS), with a purity of 86% according to HPLC (220 nm), corresponding to a yield of 87% of the theoretically possible.

The invention claimed is:

1. Method for production of N-substituted aromatic hydroxylamines of formula I:

$$R-N(OH)-C(=O)-(O)R_1 \qquad (I),$$

by a single process step of hydration of aromatic nitrogen compounds of formula II $$R-NO_2 \qquad (II),$$

with a hydration catalyst and hydrogen in an aprotic solvent, characterised in that the reaction is performed in the presence of at least stoichiometric quantities of a compound of formula III $$Y-C(=O)-(O)R_1 \qquad (III),$$

wherein R is an aromatic residue, $R_1$ a hydrocarbon residue and Y is halogen.

2. Method according to claim 1, characterised in that the group R comprises aromatic hydrocarbons or heteroaromatics, or condensed or linked ring systems, and the group R is unsubstituted or substituted.

3. Method according to claim 1, characterised in that $R_1$ stands for linear or branched $C_1$-$C_8$-alkyl, $C_3$-$C_8$-cycloalkyl, benzyl or phenyl.

4. Method according to claim 1, characterised in that the compounds of formula III are $C_1$-$C_4$-alkyl-O—CO—Cl.

5. Method according to claim 1, characterised in that the compounds of formula III are chloroformic acid methylester.

6. Method according to claim 1, characterised in that it is performed in the presence of an inert aprotic and apolar or polar solvent.

7. Method according to claim 1, characterised in that water is added to the reaction mixture.

8. Method according to claim 1, characterised in that the catalyst is a platinum catalyst.

9. Method according to claim 1, characterised in that the noble metal catalysts are used in quantities of 0.1 to 10% by weight relative to the substrate.

10. Method according to claim 1, characterised in that modifiers are added to the catalyst or to the reaction mixture.

11. Method according to claim 10, characterised in that tertiary amines, phosphorus compounds or sulphur compounds or mixtures thereof are added as modifiers.

12. Method according to claim 11, characterised in that the phosphorus compounds are selected from the group of phosphines, phosphine oxides and phosphoric acids.

13. Method according to claim 12, characterised in that the phosphorus compound is hypophosphoric acid $H_3PO_2$.

14. Method according to claim 11, characterised in that the sulphur compounds are selected from the group sulphides, thiols, thioethers, sulphoxides, thioureas and aromatic sulphur compounds.

15. Method according to claim 12, characterised in that the sulphur compound is dimethyl sulphoxide.

16. Method according to claim 1, characterised in that as a catalyst, platinum on carbon (Pt/C) is used in combination with dimethyl sulphoxide and/or hypophosphoric acid $H_3PO_2$.

17. Method according to claim 13, characterised in that the hypophosphoric acid or its derivative is used in the ratio of modifier to catalyst of 0.01-20 to 1 part by weight, preferably 0.1-5 to 1 catalyst part by weight.

18. Method according to claim 15, characterised in that dimethyl sulphoxide is used in the ratio of 0.1-20 to 1 part by weight, preferably 1-6 to 1 catalyst part by weight.

19. Method according to claim 1, characterised in that a compound of formula A

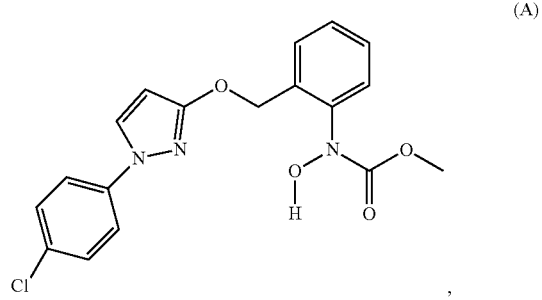 [SMILES: COC(=O)N(O)c1ccccc1COc1ccn(-c2ccc(Cl)cc2)n1]

(A)

is produced by catalytic hydration of the corresponding nitrogen compound of formula B

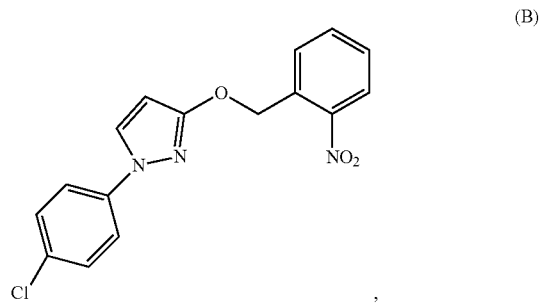 [SMILES: O=[N+]([O-])c1ccccc1COc1ccn(-c2ccc(Cl)cc2)n1]

(B)

with hydrogen in the presence of a noble metal or base metal catalyst in an inert solvent and in the presence of an inorganic base, characterised in that it is performed in the presence of at least stoichiometric quantities of chloroformic acid methylester of the formula methyl-O—C(=O)—Cl.

20. Method according to claim 1, characterised in that N-methyl-hydroxy-(phenyl) carbamate is produced by hydration of 2-nitrobenzene nitrobenzene with hydrogen in the presence of a noble metal or base metal catalyst in an inert solvent and in the presence of an inorganic base, characterised in that it is performed in the presence of at least stoichiometric quantities of chloroformic acid methylester.

* * * * *